United States Patent
Sur et al.

(10) Patent No.: US 11,806,471 B2
(45) Date of Patent: Nov. 7, 2023

(54) POWER SUPPLY FOR AN AEROSOL DELIVERY DEVICE

(71) Applicant: RAI Strategic Holdings, Inc., Winston-Salem, NC (US)

(72) Inventors: Rajesh Sur, Winston-Salem, NC (US); Stephen B. Sears, Siler City, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 297 days.

(21) Appl. No.: 17/150,512

(22) Filed: Jan. 15, 2021

(65) Prior Publication Data
US 2021/0127756 A1 May 6, 2021

Related U.S. Application Data

(63) Continuation of application No. 14/918,926, filed on Oct. 21, 2015, now Pat. No. 10,918,134.

(51) Int. Cl.
*A61M 15/06* (2006.01)
*H05B 1/02* (2006.01)
(Continued)

(52) U.S. Cl.
CPC ............. *A61M 15/06* (2013.01); *A24F 40/50* (2020.01); *A24F 40/90* (2020.01); *A61M 11/042* (2014.02);
(Continued)

(58) Field of Classification Search
CPC .... H05B 1/0202; H05B 3/0014; A61M 15/06; A61M 11/042; A61M 2016/0018;
(Continued)

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

Taiyo Yuden Co., Ltd., "Taiyo Yuden's New Hybrid Lithium Ion Capacitors Provide Energy Densities Up to 10 Times Greater than EDLCs", Press Releases, Retrieved from the Internet <URL: http://www.t-yuden.com/news/Pid=166_detail.html>, Nov. 21, 2016. 2 pages.
(Continued)

*Primary Examiner* — Brian W Jennison
(74) *Attorney, Agent, or Firm* — Womble Bond Dickinson (US) LLP; Chris Humphrey; John V. Forcier

(57) ABSTRACT

A control body is coupled or coupleable with a cartridge to form an aerosol delivery device, with the cartridge being equipped with a heating element. The control body includes a power source and a microprocessor. The power source is connected to an electrical load that includes the heater when the control body is coupled with the cartridge, and includes a supercapacitor configured to provide power to the electrical load. The microprocessor is configured to operate in an active mode in which the control body is coupled with the cartridge. In the active mode, the microprocessor is configured to direct power from the supercapacitor to the heating element to activate and vaporize components of the aerosol precursor composition.

12 Claims, 5 Drawing Sheets

(51) Int. Cl.
  *H05B 3/00* (2006.01)
  *A61M 11/04* (2006.01)
  *A24F 40/50* (2020.01)
  *A24F 40/90* (2020.01)
  *A61M 16/00* (2006.01)
  *H02J 7/34* (2006.01)
  *A24F 40/10* (2020.01)

(52) U.S. Cl.
  CPC ......... *H05B 1/0202* (2013.01); *H05B 3/0014* (2013.01); *A24F 40/10* (2020.01); *A61M 2016/0018* (2013.01); *A61M 2016/0027* (2013.01); *A61M 2016/0033* (2013.01); *A61M 2205/82* (2013.01); *A61M 2205/8206* (2013.01); *A61M 2205/8212* (2013.01); *A61M 2205/8262* (2013.01); *H02J 7/345* (2013.01)

(58) Field of Classification Search
  CPC .. A61M 2016/0027; A61M 2016/0033; A61M 2205/82; A61M 2205/8206; A61M 2205/8212; A61M 2205/8262; A24F 40/90; A24F 40/50; A24F 40/10
  See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B2 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,750,606 B2 | 7/2010 | Rusan et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0067139 A1 | 3/2007 | Kobayashi et al. |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Heibrich et al. |
| 2009/0126745 A1 | 5/2009 | Hon |
| 2009/0179613 A1* | 7/2009 | Masho ............... H02M 3/1582 320/167 |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0222195 A1* | 9/2011 | Benoit ............... H01R 13/70 361/45 |
| 2011/0265806 A1 | 11/2011 | Alarcon et al. |

(56) References Cited

U.S. PATENT DOCUMENTS

| | | |
|---|---|---|
| 2011/0309157 A1 | 12/2011 | Yang et al. |
| 2012/0042885 A1 | 2/2012 | Stone et al. |
| 2012/0050950 A1* | 3/2012 | Kim .................. H01G 11/50 361/505 |
| 2012/0060853 A1 | 3/2012 | Robinson et al. |
| 2012/0068626 A1 | 3/2012 | Lekatsas et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0104916 A1 | 5/2013 | Bellinger et al. |
| 2013/0192619 A1 | 8/2013 | Tucker et al. |
| 2013/0199528 A1* | 8/2013 | Goodman ......... A61M 15/0091 392/394 |
| 2013/0220315 A1 | 8/2013 | Conley et al. |
| 2013/0243410 A1 | 9/2013 | Nichols et al. |
| 2013/0255702 A1 | 10/2013 | Griffith, Jr. et al. |
| 2013/0298905 A1 | 11/2013 | Levin et al. |
| 2013/0300204 A1 | 11/2013 | Partovi |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0014125 A1 | 1/2014 | Fernando et al. |
| 2014/0041655 A1 | 2/2014 | Barron et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0224267 A1 | 8/2014 | Levitz et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0283855 A1 | 9/2014 | Hawes et al. |
| 2014/0299137 A1 | 10/2014 | Kieckbusch et al. |
| 2014/0345631 A1 | 11/2014 | Bowen et al. |
| 2015/0007838 A1 | 1/2015 | Fernando et al. |
| 2015/0053217 A1 | 2/2015 | Steingraber et al. |
| 2015/0357839 A1 | 12/2015 | Cai et al. |
| 2016/0037826 A1 | 2/2016 | Hearn et al. |
| 2016/0148759 A1 | 5/2016 | El-Kady et al. |

FOREIGN PATENT DOCUMENTS

| | | |
|---|---|---|
| CN | 1339616 A | 3/2002 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 101414790 A | 4/2009 |
| CN | 201379072 | 1/2010 |
| CN | 201690263 | 12/2010 |
| CN | 101965677 A | 2/2011 |
| CN | 201758279 U | 3/2011 |
| CN | 102655976 A | 9/2012 |
| CN | 202872445 U | 4/2013 |
| CN | 103098554 | 5/2013 |
| CN | 203121009 | 8/2013 |
| CN | 103339844 A | 10/2013 |
| CN | 103501847 | 1/2014 |
| CN | 203398814 | 1/2014 |
| CN | 203606832 | 5/2014 |
| CN | 103917119 | 7/2014 |
| CN | 204030686 U | 12/2014 |
| CN | 204166110 U | 2/2015 |
| CN | 204334024 | 5/2015 |
| CN | 104715709 A | 6/2015 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 081 275 | 7/2009 |
| EP | 2 100 525 | 9/2009 |
| EP | 2 316 286 | 5/2011 |
| GB | 2469850 | 11/2010 |
| JP | 07-095766 A | 4/1995 |
| JP | 2004254401 A | 9/2004 |
| JP | 2011515080 A | 5/2011 |
| JP | 2012244164 A | 12/2012 |
| KR | 20160103425 A | 9/2016 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2012/120487 | 9/2012 |
| WO | WO 2013/089551 | 6/2013 |
| WO | WO 2013/138384 | 9/2013 |
| WO | WO-2013180661 A1 | 12/2013 |
| WO | WO-2015107551 A2 | 7/2015 |
| WO | WO 2015/127429 | 8/2015 |
| WO | WO-2015115417 A1 | 8/2015 |
| WO | WO 2016/118005 | 7/2016 |

OTHER PUBLICATIONS

Jun Liu, et al., "Hybrid Power Supply and Its Application in Electric Vehicles," Proceedings of the 27th Annual Academic Conference of Electric Power System and Automation in Chinese Universities, Oct. 15, 2011, 6 pages.

* cited by examiner

POWER SUPPLY FOR AN AEROSOL DELIVERY DEVICE

CROSS-REFERENCE TO RELATED APPLICATIONS

This application is a Continuation of U.S. patent application Ser. No. 14/918,926, filed Oct. 21, 2015, entitled Power Supply for an Aerosol Delivery Device, the contents of which are hereby incorporated by reference.

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference.

BRIEF SUMMARY

The present disclosure relates to aerosol delivery devices, methods of forming such devices, and elements of such devices. The present disclosure includes, without limitation, the following example implementations. In some example implementations, a control body is provided. The control body is coupled or coupleable with a cartridge that is equipped with a heating element and contains an aerosol precursor composition, the control body being coupleable with the cartridge to form an aerosol delivery device in which the heating element is configured to activate and vaporize components of the aerosol precursor composition. The control body comprises a power source and a microprocessor. The power source is connected to an electrical load that includes the heater when the control body is coupled with the cartridge, and the power source includes a supercapacitor configured to provide power to the electrical load. The microprocessor is configured to operate in an active mode in which the control body is coupled with the cartridge. The microprocessor in the active mode is configured to direct power from the supercapacitor to the heating element to activate and vaporize components of the aerosol precursor composition.

In some example implementations of the control body of the preceding or any subsequent example implementation, or any combination thereof, the supercapacitor is an electric double-layer capacitor (EDLC).

In some example implementations of the control body of any preceding or any subsequent example implementation, or any combination thereof, the supercapacitor is a hybrid capacitor such as a lithium-ion capacitor (LIC).

In some example implementations of the control body of any preceding or any subsequent example implementation, or any combination thereof, the power source further comprises a snubber circuit connected in parallel with the supercapacitor.

In some example implementations of the control body of any preceding or any subsequent example implementation, or any combination thereof, the power source further comprises a DC-to-DC converter connected to the supercapacitor, between the supercapacitor and electrical load.

In some example implementations of the control body of any preceding or any subsequent example implementation, or any combination thereof, the power source further comprises a diode connected to the electrical load, between the supercapacitor and electrical load.

In some example implementations of the control body of any preceding or any subsequent example implementation, or any combination thereof, the power source further comprises a DC-to-DC converter connected to the supercapacitor, between the supercapacitor and electrical load; and a diode connected to, and between, the DC-to-DC converter and electrical load.

In some example implementations of the control body of any preceding or any subsequent example implementation, or any combination thereof, the DC-to-DC converter has an input and output, and the diode has an anode and a cathode, and wherein the input and output of the DC-to-DC converter are connected to respectively the supercapacitor and the anode of the diode, and the cathode of the diode is connected to the electrical load.

In some example implementations of the control body of any preceding or any subsequent example implementation, or any combination thereof, the power source further comprises a snubber circuit connected in parallel with the supercapacitor and thereby forming a parallel combination, the DC-to-DC converter being connected in series with the parallel combination of the snubber circuit and supercapacitor.

In some example implementations of the control body of any preceding or any subsequent example implementation, or any combination thereof, the power source further comprises terminals connectable with a source of energy from which the supercapacitor is chargeable.

In some example implementations of the control body of any preceding or any subsequent example implementation, or any combination thereof, the power source further comprises the source of energy, and the source of energy is or includes a solid-state battery.

In some example implementations of the control body of any preceding or any subsequent example implementation, or any combination thereof, the power source further comprises the source of energy, and the source of energy is or includes a lithium-ion battery.

In some example implementations of the control body of any preceding or any subsequent example implementation, or any combination thereof, the power source further comprises a DC-to-DC converter connected to the supercapacitor, between the supercapacitor and electrical load.

In some example implementations of the control body of any preceding or any subsequent example implementation, or any combination thereof, the power source further comprises a diode connected to the source of energy, between the source of energy and supercapacitor.

In some example implementations of the control body of any preceding or any subsequent example implementation, or any combination thereof, the power source further comprises a DC-to-DC converter connected to the supercapacitor, between the supercapacitor and electrical load; and a diode connected to, and between, the source of energy and DC-to-DC converter.

In some example implementations of the control body of any preceding or any subsequent example implementation, or any combination thereof, the DC-to-DC converter has an input and output, and the diode has an anode and a cathode, and wherein the input and output of the DC-to-DC converter are connected to respectively the supercapacitor and the cathode of the diode, and the anode of the diode is connected to the source of energy.

In some example implementations of the control body of any preceding or any subsequent example implementation, or any combination thereof, the power source further comprises a snubber circuit connected in parallel with the supercapacitor and thereby forming a parallel combination, the DC-to-DC converter being connected in series with the parallel combination of the snubber circuit and supercapacitor.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
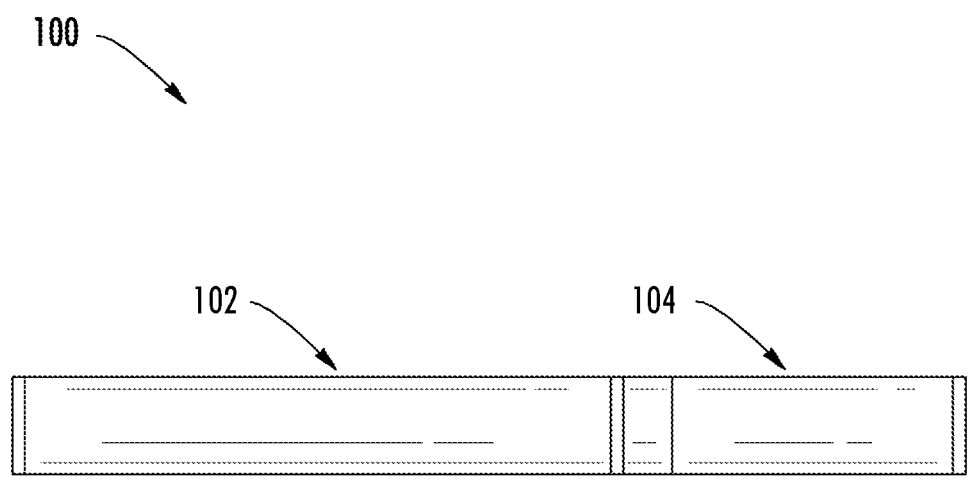
FIG. 1 illustrates a side view of an aerosol delivery device including a cartridge coupled to a control body according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or capacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular or rhomboidal in cross-section, which may lend itself to greater compatibility with a substantially flat or thin-film power source, such as a power source including a flat battery. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical alternating current electrical outlet, connection to a car charger (i.e., a cigarette lighter receptacle), connection to a computer, such as through a universal serial bus (USB) cable or connector, or connection to a photovoltaic cell (sometimes referred to as a solar cell) or solar panel of solar cells. Further, in some example implementations, the cartridge may comprise a single-use cartridge, as disclosed in U.S. Pat. No. 8,910,639 to Chang et al., which is incorporated herein by reference in its entirety.

Figure 2:
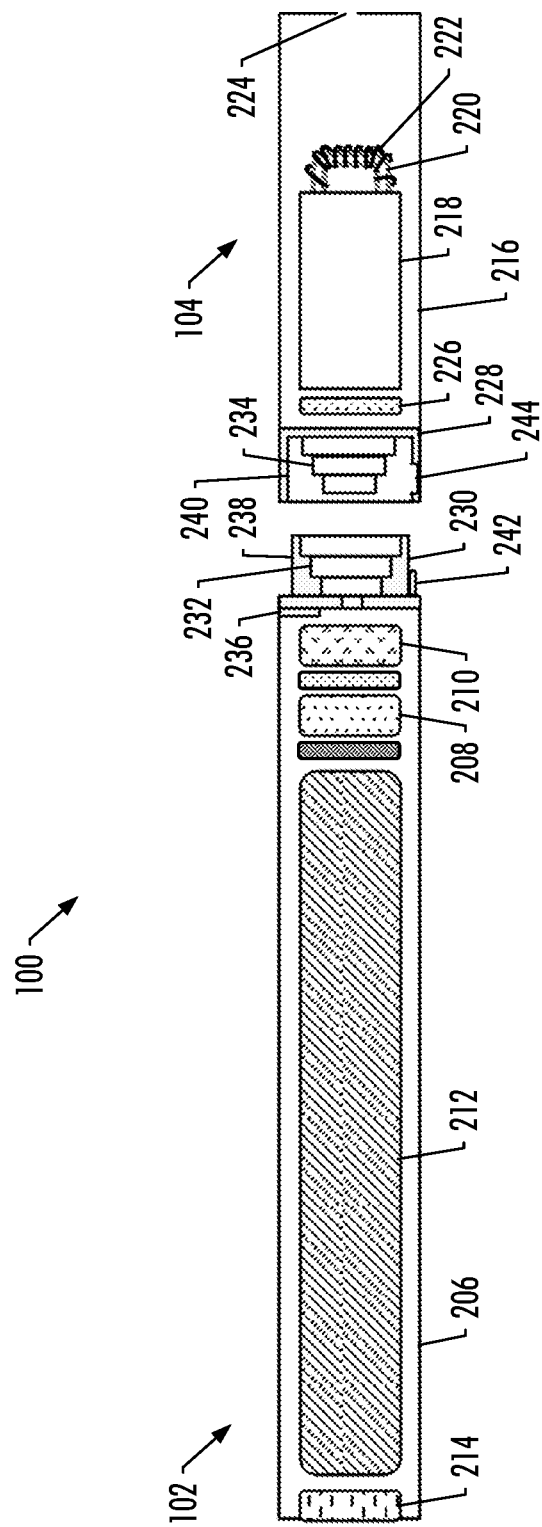
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG.

2 are representative of the components that may be present in a control body and cartridge and are not intended to limit the scope of components that are encompassed by the present disclosure. As shown, for example, the control body can be formed of a control body shell 206 that can include a control component 208 (e.g., a microprocessor, individually or as part of a microcontroller), a flow sensor 210, a power source 212 and one or more light-emitting diodes (LEDs) 214, and such components can be variably aligned. The LED may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED.

The cartridge 104 can be formed of a cartridge shell 216 enclosing a reservoir 218 that is in fluid communication with a liquid transport element 220 adapted to wick or otherwise transport an aerosol precursor composition stored in the reservoir housing to a heater 222 (sometimes referred to as a heating element). In some example, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be a resistive heating element such as a wire coil, microheater or the like. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend) to allow for egress of formed aerosol from the cartridge 104.

The cartridge 104 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection and under-voltage lock out. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off power to the heater when the aerosol delivery device is not be drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd.

Also desirable are the so-called "smoke juices" for electronic cigarettes that have been available from Johnson Creek Enterprises LLC.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. The electronic components may include a microprocessor or processor core, and a memory. In some examples, the control component may include a microcontroller with integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

Figure 3:
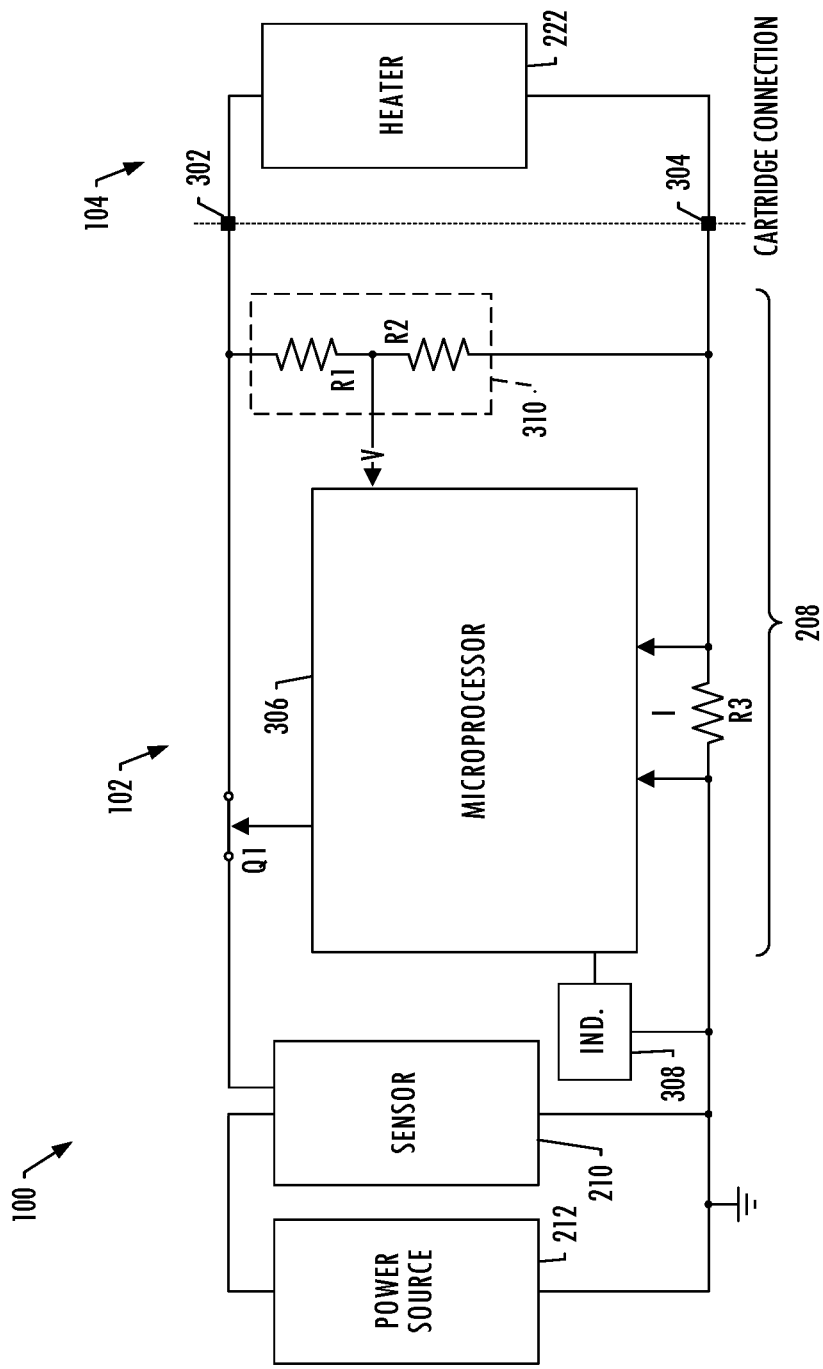
FIG. 3 illustrates various elements of a control body and cartridge of the aerosol delivery device, according to various example implementations.
Figure 4:
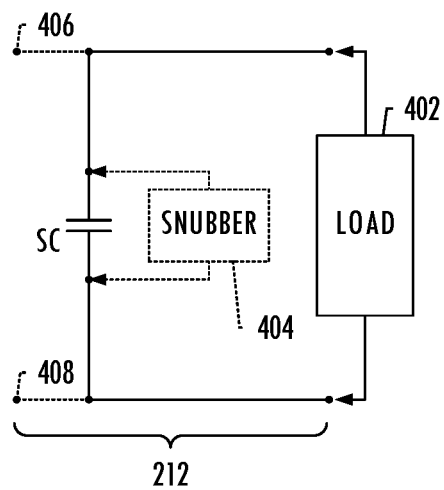
FIGS. 4-7 more particularly illustrate a power source of the control body, according to various example implementations of the present disclosure.

In accordance with some example implementations, the control component 208 may be configured to control one or more functional elements of the aerosol delivery device 100 in different states of the device. FIG. 3 illustrates the control body 102 coupled with the cartridge 104 in an active mode. As shown, the control body may include positive and negative terminals 302, 304 connectable with corresponding terminals of the heater 222 (heating element). The control component 208 may include a microprocessor 306 and a number of other electrical components, such as resistors, capacitors, switches and the like, which may be coupled with the power source 212 and heater to form an electrical circuit. In some examples, the heater may include a communication terminal for communicating data such as the puff count.

In accordance with example implementations of the present disclosure, the microprocessor 306 may be configured to measure the voltage at the positive terminal 302 and control power to the heater 222 based thereon. In some examples, the microprocessor may also control operation of at least one functional element of the aerosol delivery device 100 based on the voltage at the positive terminal. One example of a suitable functional element may be an indicator 308 such as a visual, audio or haptic indicator.

The microprocessor 306 may operate on the actual voltage at the positive terminal 302, or an analog-to-digital converter (ADC) may be included to convert the actual voltage to a digital equivalent. In some examples, the ADC may be rated for a maximum voltage less than the maximum that may be present at the positive terminal. In these examples, the control component 208 may include a voltage divider 310 configured to reduce the voltage to the microprocessor. As shown, for example, the voltage divider may include resistors R1 and R2, and may be connected to, and positioned between, the positive terminal and microprocessor, referenced to ground. The microprocessor may be configured to measure the voltage at the positive terminal from the voltage divider. In this regard, the voltage divider may include an output connected to the microprocessor and from which the microprocessor may be configured to measure the voltage at the positive terminal.

In examples in which the aerosol delivery device 100 has a housing formed of separable bodies, the aerosol delivery device, and more particularly the control component 102, may be in the standby mode when the control component is uncoupled with the cartridge 104. In examples of either a unitary or separable housing, the aerosol delivery device may be in the standby mode between puffs when the control component is coupled with the cartridge. Similarly, in examples of either a unitary or separable housing, when the user draws on the device and the flow sensor 210 detects airflow, the aerosol delivery device may be placed in the active mode during which power from the power source 212 may be directed through the sensor to power the heater 222 to activate and vaporize components of the aerosol precursor composition. In another example, power from the power source may more directly power the heater without going through the sensor (without the sensor being in-line), although the flow sensor may still detect airflow when the user draws on the device. As indicated above, power delivery from the power source may vary according to a power control mechanism; and in some examples, this power control mechanism may depend on a measured voltage at the positive terminal 302.

In the active mode in which the control body 102 is coupled with the cartridge 104 (with a unitary or separable housing), the microprocessor 306 may be configured to direct power to the heater 222 to activate and vaporize components of the aerosol precursor composition. The voltage at the positive terminal 302 may correspond to a positive heater voltage. The microprocessor may be configured to measure the positive heater voltage, such as from the voltage divider 310, and control the power directed to the heater based thereon.

In some more particular examples, the microprocessor 306 may be configured to direct power from the power source 212 (e.g., directly or through the flow sensor 210) to turn the heater 222 on and commensurately initiate a heating time period. This may include, for example, a switch Q1 between the power source (or in-line flow sensor) and the heater, which the microprocessor may operate in a closed state, as shown in FIG. 3. The microprocessor may then adjust the power directed to the heater based on the voltage at the positive terminal 302, at a periodic rate until expiration of the heating time period.

In some examples, this adjustment of power directed to the heater 222 may include the microprocessor 306 being configured to determine a moving window of measurements of instantaneous actual power directed to the heater, with each measurement of the window of measurements being determined as a product of the positive heater voltage and a current through the heater. This current may be measured in a number of different manners, such as from a current-sense resistor R3. In some examples, the microprocessor may operate on the actual current through the heater, or the control component 208 or microprocessor may include an ADC configured to convert the actual current to a digital equivalent.

The microprocessor 306 may calculate a simple moving average power directed to the heater 222 based on the moving window of measurements of instantaneous actual power, and compare the simple moving average power to a selected power set point associated with the power source 212. The microprocessor may then adjust the power directed to the heater so as to turn the heater off or on at the periodic rate at each instance in which the simple moving average power is respectively above or below the selected power set point. More information regarding aspects of the control component according to example implementations of the present disclosure may be found in the above-cited and incorporated U.S. Pat. App. Pub. No. 2014/0270727 to Ampolini et al.

FIGS. 4-7 more particularly illustrate the power source 212 according to various example implementations of the present disclosure. As shown, the power source may be connected to an electrical load 402 that includes the heater 222 when the control body 102 is coupled with the cartridge 104. More particularly, the electrical load may include the control component 208 (and its electrical components including the voltage divider 310) and heater, which explained above, may be coupled with the power source to form an electrical circuit. This may additionally include, for example, the flow sensor 210, indicator 308 and the like.

As shown, the power source 212 may include a supercapacitor SC configured to provide power to the electrical load 402. The supercapacitor may be any of a number of different types of supercapacitors, such as an electric double-layer capacitor (EDLC), a hybrid capacitor such as a lithium-ion capacitor (LIC), or the like. Supercapacitors such as EDLCs may be rated for a fast charge (e.g., three seconds). The supercapacitor be rated for a long lifetime (e.g., 32 years) and cycle life (e.g., 1,000,000 charge-discharge cycles), and provide an environmentally-friendly, lower-cost solution. The supercapacitor may provide high-current pulses to the electrical load. And as the supercapacitor does not include an electrolyte between the electrodes, the supercapacitor may therefore operate with only a negligible probability of a short circuit.

Hybrid capacitors such as the LIC generally have features of a battery (high voltage and high energy density), while maintaining the traditional characteristics of a capacitor of rapid charge (e.g., three seconds). A hybrid capacitor may be rechargeable, and have the ability to operate on its own for a longer period without the need of another source of energy from which the hybrid capacitor may be chargeable. The hybrid capacitor may have a longer lifetime (e.g., 10 years) and cycle life as compared to other options, and is more environmentally friendly.

In some examples, such as when the supercapacitor SC is or includes a hybrid capacitor such as a LIC, a snubber circuit 404 may be connected in parallel with the supercapacitor. In one example implementation, a LIC rated at 3.8 volts may include a parallel-connected snubber circuit to help maintain the LIC at least at 2.2 volts.

Figure 5:
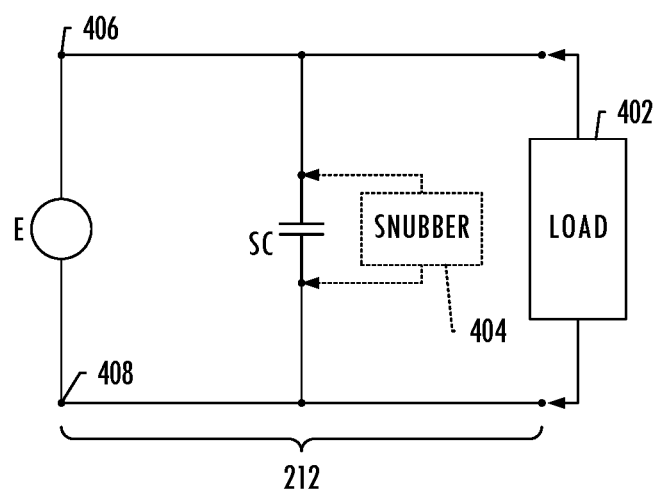

In some examples, the power source 212 may further include terminals 406, 408 connectable with a source of energy from which the supercapacitor SC may be chargeable. The source of energy may be any of a number of different types, such as various rechargers configured to operate in a manner similar to a battery charger. In other examples, the source of energy may be or include a battery. As shown in FIG. 5, in some examples, the power source may further include the source of energy E, and the source of energy may be or include a solid-state battery, lithium-ion battery or the like. In these examples, the source of energy may be fixed or removable from the power source and thus the aerosol delivery device 100.

Examples of suitable solid-state batteries are STMicroelectronics' EnFilm™ rechargeable solid-state lithium thin-film batteries, which feature a $LiCoO_2$ cathode, LiPON ceramic electrolyte and a lithium anode. In particular, the EFL700A39 battery from STMicroelectronics has a nominal voltage of 4.1V and thickness of only 220 um. The battery is rated for a 10-year life time, and a 4000 charge-discharge cycle life. The battery also has a relatively short typical charge, in some instances charging in approximately 30 minutes. The battery has a ceramic electrolyte, which may produce currents by movements of electrons and thus reduce the risk of undesirable dendrite growth in the cathode and anode that may otherwise lead to a short circuit.

In some examples and in particular those in which the source of energy E is or includes a battery, the supercapacitor SC may smooth fluctuating power from a low-current source when the source of energy weakens, and may thereby increase its lifetime and cycle life. In examples with a lithium-ion battery, the supercapacitor may operate over a larger range of temperatures (e.g., from −50 to 70° C.) than the lithium-ion battery, and may turn on at cold temperatures (e.g., below −10° C.) and high temperatures (e.g., above 40° C.) when the lithium-ion battery may otherwise fail to start. In these examples, the supercapacitor may therefore provide additional benefits in colder and warmer regions.

Figure 6:
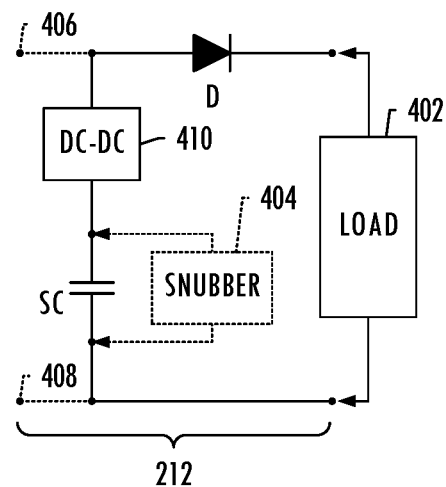
Figure 7:
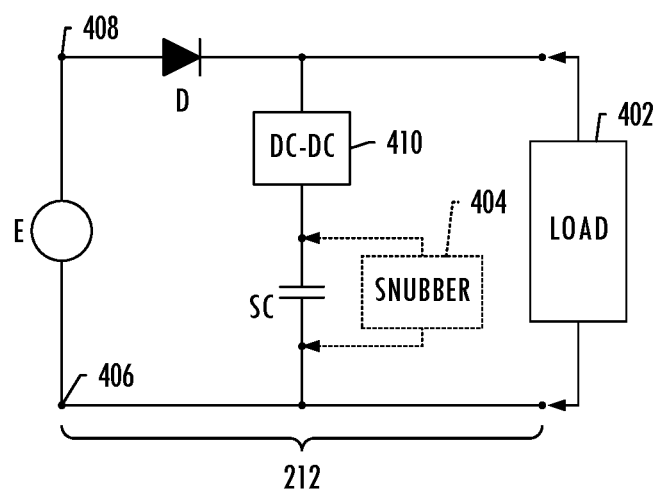

As shown in FIGS. 6 and 7, in some examples, the power source 212 may further include other components such as a DC-to-DC converter 410 and/or a diode D. FIGS. 6 and 7 illustrate the power source including both a DC-to-DC converter and diode, but it should be understood that the power source may include either without the other. The DC-to-DC converter may avoid too fast discharge of the supercapacitor SC, and it may facilitate a uniform dissipation of current so that the supercapacitor provides constant power to the electrical load 402. The diode may facilitate current flow into the electrical load, and prevent current flow back, when the capacitor is discharged.

The DC-to-DC converter 410 may be connected to the supercapacitor SC, between the supercapacitor and electrical load 402. As shown in FIG. 6, in some more particular examples, the diode D may be connected to, and between, the DC-to-DC converter and electrical load. And in at least some of these examples, an input and output of the DC-to-DC converter may be connected to respectively the supercapacitor and anode of the diode, and the cathode of the diode may be connected to the electrical load.

As shown in FIG. 7, in some examples, the diode D may be connected to, and between, the source of energy E and DC-to-DC converter 410. In at least some of these examples, the input and output of the DC-to-DC converter may be connected to respectively the supercapacitor SC and the cathode of the diode, and the anode of the diode may be connected to the source of energy. And in examples including the snubber circuit 404, as shown in FIGS. 6 and 7, the snubber circuit and supercapacitor may form a parallel combination with which the DC-to-DC converter may be connected in series.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-4 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
    an atomizer configured to produce an aerosol from an aerosol precursor composition;
    a power source connected to an electrical load that includes the atomizer, the power source comprising a supercapacitor configured to provide power to the electrical load, wherein the supercapacitor is a hybrid capacitor, wherein the power source further comprises:
    a DC-to-DC converter connected to the supercapacitor, between the supercapacitor and electrical load;
    a snubber circuit connected in parallel with the supercapacitor and thereby forming a parallel combination, the DC-to-DC converter being connected in series with the parallel combination of the snubber circuit and supercapacitor; and
    a diode connected to, and between, the DC-to-DC converter and electrical load; and
    a microprocessor configured to operate in an active mode in which the microprocessor is configured to direct power from the power source to the atomizer and thereby control the atomizer to activate and produce the aerosol.

2. The aerosol delivery device of claim 1, wherein the DC-to-DC converter has an input and output, and the diode has an anode and a cathode, and
    wherein the input and output of the DC-to-DC converter are connected to respectively the supercapacitor and the anode of the diode, and the cathode of the diode is connected to the electrical load.

3. The aerosol delivery device of claim 1, wherein the power source further comprises terminals connectable with a source of energy from which the supercapacitor is chargeable.

4. The aerosol delivery device of claim 3, wherein the power source further comprises the source of energy, and the source of energy is or includes a solid-state battery.

5. The aerosol delivery device of claim 3, wherein the power source further comprises the source of energy, and the source of energy is or includes a lithium-ion battery.

6. The aerosol delivery device of claim 3, wherein the power source further comprises a diode connected to the source of energy, between the source of energy and the supercapacitor.

7. A control body for an aerosol delivery device, the control body comprising:
    a power source connected to an electrical load, the power source comprising a supercapacitor configured to provide power to the electrical load, wherein the supercapacitor is a hybrid capacitor, wherein the power source further comprises:
    a DC-to-DC converter connected to the supercapacitor, between the supercapacitor and electrical load;
    a snubber circuit connected in parallel with the supercapacitor and thereby forming a parallel combination, the DC-to-DC converter being connected in series with the parallel combination of the snubber circuit and supercapacitor; and
    a diode connected to, and between, the DC-to-DC converter and electrical load; and
    a microprocessor configured to operate in an active mode in which the microprocessor is configured to direct power from the power source to the electrical load to cause the aerosol delivery device to produce an aerosol from an aerosol precursor composition.

8. The control body of claim 7, wherein the DC-to-DC converter has an input and output, and the diode has an anode and a cathode, and
    wherein the input and output of the DC-to-DC converter are connected to respectively the supercapacitor and the anode of the diode, and the cathode of the diode is connected to the electrical load.

9. The control body of claim 7, wherein the power source further comprises terminals connectable with a source of energy from which the supercapacitor is chargeable.

10. The control body of claim 9, wherein the power source further comprises the source of energy, and the source of energy is or includes a solid-state battery.

11. The control body of claim 9, wherein the power source further comprises the source of energy, and the source of energy is or includes a lithium-ion battery.

12. The control body of claim 9, wherein the power source further comprises a diode connected to the source of energy, between the source of energy and the supercapacitor.

* * * * *